United States Patent [19]
Rollman et al.

[11] Patent Number: 5,685,303
[45] Date of Patent: *Nov. 11, 1997

[54] APPARATUS AND METHOD FOR MEASURING ELECTRICAL ACTIVITY OF HEART

[75] Inventors: Bruce L. Rollman, 10 Timberlane Ct., Pittsburgh, Pa. 15217; Alan E. Sherman, St. Louis, Mo.

[73] Assignee: Bruce L. Rollman

[*] Notice: The term of this patent shall not extend beyond the expiration date of Pat. No. 5,370,116.

[21] Appl. No.: 307,667

[22] PCT Filed: Feb. 9, 1994

[86] PCT No.: PCT/US94/01467

§ 371 Date: Sep. 20, 1994

§ 102(e) Date: Sep. 20, 1994

[87] PCT Pub. No.: WO94/17729

PCT Pub. Date: Aug. 18, 1994

Related U.S. Application Data

[63] Continuation-in-part of Ser. No. 16,642, Feb. 12, 1993, Pat. No. 5,370,116.

[51] Int. Cl.⁶ .................................................. A61R 5/0402
[52] U.S. Cl. ............................................................ 128/644
[58] Field of Search .................................. 128/644, 639, 128/640, 656

[56] References Cited

U.S. PATENT DOCUMENTS

| | | | |
|---|---|---|---|
| 3,409,007 | 11/1968 | Fuller | 128/644 |
| 4,202,344 | 5/1980 | Mills et al. | 128/644 |
| 4,432,368 | 2/1984 | Russek | 128/644 |
| 4,763,660 | 8/1988 | Kroll et al. | 128/644 |
| 4,854,323 | 8/1989 | Rubin | 128/644 |
| 4,957,109 | 9/1990 | Groeger et al. | 128/640 |
| 5,224,479 | 7/1993 | Sekine | 128/644 |
| 5,370,116 | 12/1994 | Rollman et al. | 128/644 |

FOREIGN PATENT DOCUMENTS 274612  7/1951  Switzerland ..................... 128/644

OTHER PUBLICATIONS

Dzhogan, Biomed, Eng. 11, 319–320 (1977).

Barr, Anaesthesia, 27(1) 94–96 (1972).

*Primary Examiner*—Lee S. Cohen
*Attorney, Agent, or Firm*—Gerald S. Rosen

[57] ABSTRACT

A smooth surfaced, inelastic, flexible, S-shaped or L-shaped belt-like strip for recording electrocardiograms having a series of separate precordial electrical contacts and laterally placed separate, independently movable precordial leads and electrodes movable laterally insuring proper placement on the patient's chest or precordium during usage. The S- and/or L-shape of the strip helps cover proper recording areas. Raised, fixed, compressible precordial electrodes maintain contact with each patient's chest allowing for variations in chest size among patients. The apparatus is attached to the chest with an adjustable elastic strap providing a constant and evenly distributed downward force holding it and the precordial leads in place. Lead wires exit the lateral sides of the precordial belt-like strip towards electrodes placed on each arm. Lead wires from the precordial electrodes and from each of the left and right arm electrodes travel inside or on the outside surface of the S-shaped and/or L-shaped belt-like strip and emerge to form a main cable which connects via a suitable adapter or plug to an electrocardiograph machine. Two additional wire leads enter the cable to transmit signals from each lower limb electrode towards the main cable for transmission to the electrocardiograph machine. All limb lead wires end in male connector plugs to facilitate attachment to a variety of EKG electrodes in known use. This device is reusable for many patients, easily cleaned and designed for use with patients of a variety of body habitus' during usage.

10 Claims, 8 Drawing Sheets

LEFT & RIGHT
LEG ELECTRODES

APPARATUS AND METHOD FOR MEASURING ELECTRICAL ACTIVITY OF HEART

This is a continuation-in-part of applicants' U.S. patent application Ser. No. 08/016,642, filed Feb. 12, 1993, now U.S. Pat. No. 5,320,116.

BACKGROUND OF THE INVENTION

1. Field of Invention

This invention relates to a new, practical belt-type apparatus containing therein lead wires for measuring the electrical activity of the heart of a patient when used with an electrocardiograph machine. The belt-like apparatus is attached to a patient. It is useful in place of the conventional individual wires attached to the patient, one at a time, for taking an electrocardiogram.

An electrocardiogram, generally referred to as an ECG or an EKG, is a visual display of the electrical activity of the heart. Electrocardiograms are accepted in the field of medicine, particularly cardiology, to be of great value in the diagnosis and management of patients with heart disease, undergoing surgery, in distress for other medical reasons and undergoing routine physical examinations to establish a baseline record of the heart's electrical activity. In cases where a permanent record is desired, the EKG is usually recorded by an electrocardiograph machine on paper made especially for that purpose.

The most commonly performed electrocardiogram is called a "twelve-lead EKG" although it is made with only 10 separate lead wires attached to electrodes that are attached to the body of the patient. Six of the electrodes are attached to the patient's chest at certain known recording zones over the heart. They and their attached lead wires are referred to as the "precordial" electrodes and leads, respectively. Four other wires and their attached electrodes are commonly referred to as the "limb" electrodes and leads, respectively. Each limb of the patient has a corresponding limb lead with its electrode attached thereto over commonly accepted recording zones. Such electrodes must be applied one at a time and in the particular case of the precordial electrodes must be placed in the proper sequence over the proper recording area for each lead. In addition, the two arm leads must not be reversed in order to avoid obtaining a faulty EKG tracing (this is not critical for the leg leads). Because of the great number of separate leads and their length, problems with conventional devices often arise, e.g., the wire leads frequently get entangled during normal usage resulting in time delays to perform the next EKG and wires are mistakenly placed over the wrong recording area of the body leading to inaccurate readings requiring repeating the test or else untoward errors in patient care and management may result. These events may not only place the patient in potential harm, but also waste the time of the patient, performing technician, and attending physician, thus adding to the cost of medical care.

Conventional precordial EKG electrodes are applied to the body with either suction cups or self-adhesive disposable electrodes. Both devices are prone to falling off, for example, when the patient is large breasted and/or its chest is hairy, sweaty, and/or the test is performed with the patient partly or completely sitting up. Such circumstances generally lead to additional delay in performing the test. In addition, the reusable suction cups may become unsightly or unsanitary through use particularly when employed in a high volume patient setting such as an emergency room.

2. Prior Art

The prior art reveals several alternative devices for recording EKGs. Mills et al. U.S. Pat. Nos. 4,121,575 and 4,202,433 teach embedding the precordial electrodes in an elastic strip held down by weights at both ends. However, the entire device is not contoured to accommodate patients with large pectoral muscles or breasts nor can it accommodate those who cannot lie completely flat during the test. The greatest interpersonal variability in the distances between patients' precordial recording zones occurs laterally because of the downward curvature of the chest approaching the left flank. Mills et al. fail to take this variability into account by fixing the positions of V4, V5 and V6 thus limiting the variety of chest sizes with which it may be used. In addition, weights applied at both ends will tend to lift the centermost electrodes off the chest leading to incomplete recordings from one or more of the central precordial electrodes. Further, neither of the Mills et al. patents describe recording signals from any of the limb leads.

Arkans, U.S. Pat. No. 4,328,814, describes a precordial strip of six electrodes that are self-adhesive and adjustable to accommodate a wide variety of body habitus'. In addition, the entire device is removably attached to a particular plug from an EKG machine. As with conventional precordial electrodes, the adhesive may not properly stick to patients' precordiums for the reasons described above. In addition, the adhesive electrodes are not reusable and the device does not record signals from the limb leads.

Rubin, U.S. Pat. No. 4,854,323, like Mills et al., describes placing the precordial electrodes in a fixed sequence to avoid electrode reversals. In addition, all six of the electrodes are freely movable along a shapable track to accommodate a variety of body habitus'. However, since there is little or no downward pressure exerted on the chest throughout the normal respiratory cycle, all of the precordial electrodes may not be in simultaneous contact with the chest during recording due to the stiffness of the tube and/or stylet. Further, there are no fixed distances between the locations of any of the precordial leads. This might decrease the intrapersonal reproducibility of the EKG as all precordial electrodes are freely movable. Similar to Arkans, all of the leads exit the device in a cable ending in a plug making for easy attachment to an EKG device. Rubin's invention is intended to be reusable, yet the complex shapes of its parts hinder easy cleaning between patient use. Finally, the disclosed device also does not record signals from the limb leads.

Groeger et al., U.S. Pat. No. 4,957,109, as in the Mills et al. and Arkans teachings, does not disclose significant interpersonal variation in the distances between the lateral precordial recording zones. However, adjustments can be made between patients of various sizes by making kinks in the flexible conductors. The electrodes are attached to the body by an electrically conductive adhesive that is similar to conventional methods using disposable electrodes. The adhesive used may not properly stick to patients' precordiums resulting in poor EKG tracings for the reasons described above. The Groeger et al. device may be used with the wireless telemetry device described in the patent or hard wired to provide automatic or continuous EKG monitoring. In addition, its parts are only partly reusable after each patient.

There is, therefore, a need for an EKG signal recording device that at once provides an accurate, effective, efficient, hygienic, and reusable means of recording EKG's.

SUMMARY OF THE INVENTION

The electrocardiogram apparatus of this invention solves the problems of presently used methods of recording EKGs.

The apparatus of this invention comprises a smooth surfaced, flexible, inelastic belt-like strip structure sufficiently wide from top to bottom to accommodate lead wires therein and sufficiently long from a first end to a second end to enable it to be attached around a patient's chest. The belt-like strip has a shape that is attachable to and follows the contours of the chest of the patient. Examples of typical lengthwise configurations along the top and bottom edges of the belt-like strip are an S-like and an L-like configuration, although other configurations are within the scope of this invention. The preferred embodiments are either S-like or L-like configurations. At one end of the belt-like strip is an adjustable fastener element, preferably an easily removable elastic strip, that attaches to an easily removable fastener, preferably an adjustable elastic strip, at the second end of the belt-like strip. Other conventional elastic or adjustable fasteners can also be used. The elastic strip is of sufficient length and elasticity so that it is adjustable to accommodate a variety of patients' chest circumferences. The elasticity of the fastener element is sufficient to provide the tension required to hold the belt-like structure in place against the patient's chest during normal respiration and if the patient is unable to lie flat during the EKG recording procedure. The smooth surfaced, inelastic, flexible, belt-like strip has three fixed, raised electrode-contact structures fixedly attached on the back surface of the belt-like strip, i.e. the surface which contacts the patient, at appropriately spaced apart locations designated $V_1$, $V_2$ and $V_3$. Each raised, fixed electrode is preferably compressible and makes contact over each of the first three consecutive precordial recording zones of the patient. Three flexible and independently movable wire leads with attached electrodes exit from three other spaced apart locations on the smooth surfaced, inelastic, flexible, belt-like strip lateral to the fixed electrodes and, in a preferred embodiment, lateral to the preferred S-like or L-like curvature, to provide the remaining three precordial leads to the precordial zones designated $V_4$, $V_5$ and $V_6$ respectively. The movable wire leads with electrodes, in a preferred embodiment, are placed on the zones $V_4$, $V_5$ and $V_6$ between the back surface of the belt-like strip and the chest. This holds the electrodes firmly against the precordial zones. In some cases it might be necessary to place one or more of the leads on the patient's chest above the upper edge of the belt-like strip. One wire lead exits from each lateral side of the device and records the limb lead signals from each arm. They are referred to commonly, as "RA" and "LA", for the right and left arms respectively. Two other wires bifurcate from a point on a cable exiting the strip to comprise the remaining limb leads and are commonly referred to as "RL" and "LL" for the right and left legs respectively. The wires leading to each arm and leg from the flexible strip and cable extend sufficiently for their electrodes to achieve electrical contact with the appropriate limb. A connector plug on the ends of each of the limb leads, preferably a male circular connector plug, although other shapes of connector plugs are suitable, attaches to each limbs' recording electrode. A variety of limb recording electrodes currently available and in use may be used with the device's connector plugs including a snap type electrode as disclosed in Healy U.S. Pat. No. 4,331,153, alligator clip type electrode, belt type electrode or clamp type electrode among other means at the discretion of the operator.

The three fixed anterior precordial electrodes for the first three precordial recording zones, $V_1$, $V_2$ and $V_3$, are applied appropriately over known central chest or thoracic body surface landmarks corresponding to those first three precordial recording zones. The location of the electrode for the $V_1$ position can be indicated on the front surface of the belt-like strip to aid in properly placing the belt-like strip on the patient's chest, indicia can also be located on the front surface of the belt-like strip to aid in locating the $V_2$ and $V_3$ positions. The electrodes are raised from the back surface of the belt-like structure to allow contact with the central portions of the precordium regardless of the size of the patient's pectoral muscles or breasts. This is necessary because lateral forces exerted when the smooth surfaced, inelastic, flexible, belt-like strip is fastened around the body tend to vertically lift the anterior central portion of the strip off the central precordium. In addition, the raised and fixed precordial electrodes are preferably mounted on compressible, preferably rubber or foam filled projections, to enable the electrodes to make contact that is appropriately contoured to the body over muscles and breasts. The remaining three independently movable precordial electrode wires are each long enough to enable the electrodes thereon to make contact with the proper body surface recording areas found in a wide variety of patient body habitus'. The electrodes thereon usually and preferably are between the back surface of the belt-like strip and the chest. The movable electrode leads generally are not long enough to overlap each other and thus are prevented from entangling.

After the smooth surfaced, inelastic, flexible, belt-like structure is applied to the chest with the fixed precordial electrodes in proper alignment over the appropriate recording zones, the apparatus is fastened to the chest by coupling the free end of the elastic fastener strip on one end of the belt-like structure to a closure attached to the second end of the inelastic, flexible, belt-like structure directly or via an elastic strip and preferably located on the end nearest to the $V_1$ electrode, although the elastic fastener strip can be on the second end and the closure can be on the first end of the belt-like strip. Any suitable closure can be used, e.g. Velcro, snap, buckle and the like, Velcro is preferred because it can be easily and quickly opened. A relatively constant downward force toward the patient's chest is thereby generated sufficient to hold the entire precordial apparatus, including the precordial electrodes, which are between the smooth surface, inelastic, flexible belt-like structure and the patient's chest, in proper position throughout the patient's normal respiratory cycle. The pressure of the evenly distributed downward forces keeps all the precordial electrodes in place securely over the precordium and is not affected by the presence of a hairy or sweaty chest. In addition, the downward forces keep the precordial electrodes in place even if the patient cannot lie completely flat during the EKG recording procedure. Optionally, the smooth surfaced, flexible, inelastic, belt-like structure can also have a shoulder strap to aid in holding it in place. Preferably, the shoulder strap is on the patient's right shoulder and held in place by a fastener such as a snap or Velcro. The shoulder strap can be a loop around the shoulder or can go over the shoulder and held on the elastic strip in back by Velcro or a loop.

After the elastic fastener strip is fastened, in the most preferred embodiment, the remaining independently movable precordial leads are positioned between the smooth surfaced, flexible, inelastic, belt-like structure and their proper recording zones on the precordium. They are kept in proper position by the constant downward forces exerted on the inelastic belt by the elastic strip once it is fastened. A suitable amount of an electrolyte conducting paste is then applied to each of the six precordial electrodes on the surface facing the chest wall. Finally, each limb lead is applied, using additional electrolyte paste before the operator records the 12-lead EKG. The apparatus thus ensures that the precordial and upper body limb leads are never applied in an incorrect sequence. The two lead wires and electrodes that attach to each of the patient's legs, "RL" and "LL" respectively, may in fact be inadvertently reversed without adversely affecting the EKG tracing.

Wires attached to and leading from the fixed and movable precordial electrodes and arm limb leads are within or on a surface of the smooth surfaced, inelastic, flexible, belt-like structure and emerge from it at a convenient point to form a cable. The cable may have an adapter or plug at its free terminus for connection to an electrocardiograph machine or to any appropriate adapter, plug, junction box or block exiting from the electrocardiograph machine. The only requirement is that all the wires comprising the cable are connected to the correct corresponding wire or electrical contact from the EKG machine. In its preferred embodiments, the position of the cable's exit from the smooth surfaced, inelastic, flexible, S-shaped or L-shaped belt-like structure is near the base of the anteriorly placed S- or L-shaped configuration to center weight the device once placed on the precordium.

The smooth surfaced, inelastic, flexible, belt-like structure can be made of non-conductive plastic or any other polymer including rubber or rubberized material or some combination of these materials to enable easy cleaning. The fixed and movable electrodes, leads and wires may be made of any suitable electrically-conductive metal and properly insulated. The main cable can be disconnected from the smooth surfaced, inelastic, flexible, belt-like structure for ease of cleaning the belt and its electrodes. The device of this invention can be easily cleaned after each use for subsequent use by many patients. The smooth surfaces of all parts that come into contact with patients during usage facilitate easy cleaning with liquid germicidal agents.

The invention, thus, provides a reusable apparatus that enables the operator to take EKG's accurately, effectively, efficiently and hygienically.

BRIEF DESCRIPTION OF THE DRAWINGS

FIG. 5b is a front view of the movable electrode shown in FIG. 5a;

FIG. 5c is a side view of the movable electrode shown in FIG. 5a;

DETAILED DESCRIPTION

Figure 1:
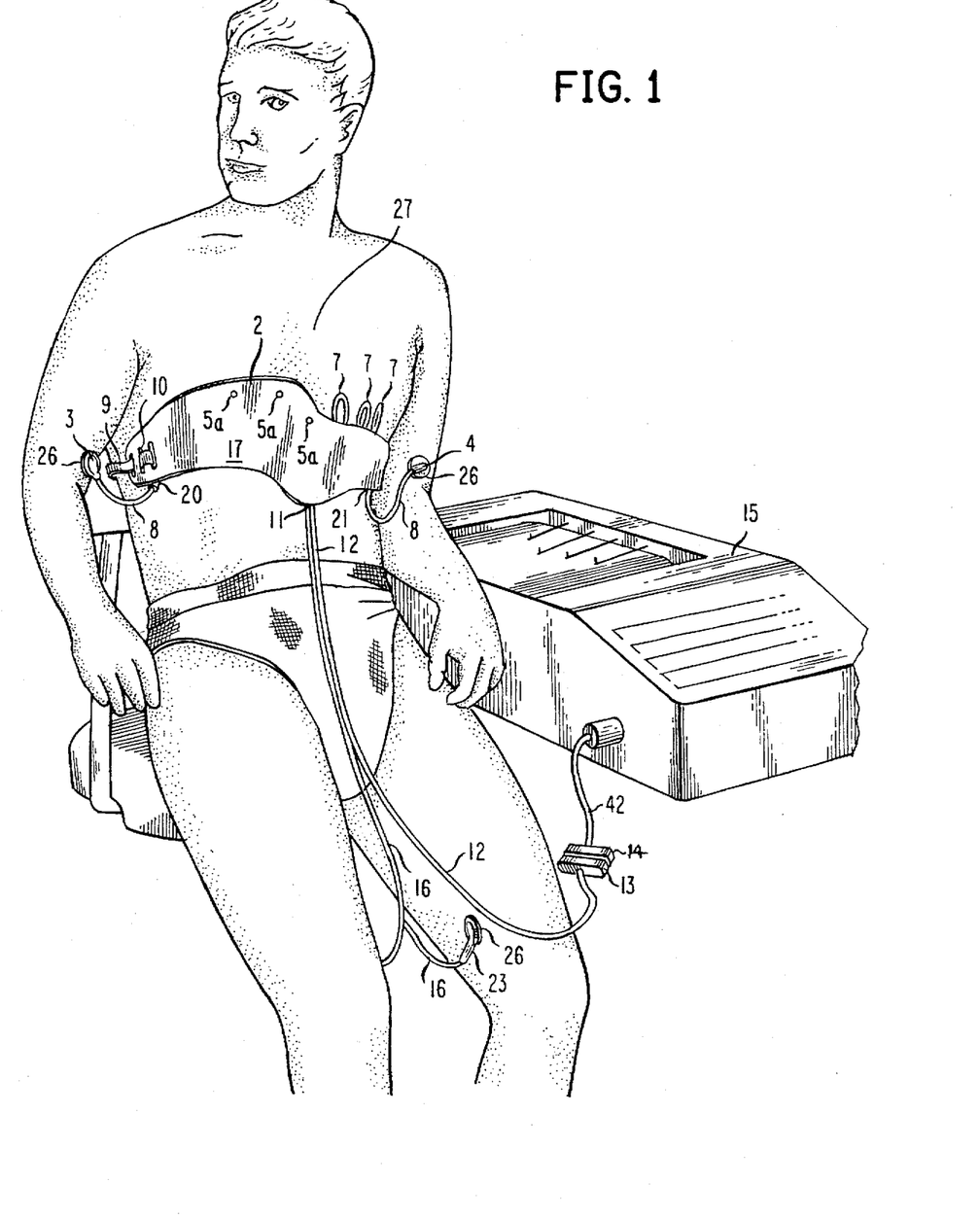
FIG. 1 depicts one embodiment of the electrocardiogram device of the invention placed on a patient and connected to an electrocardiograph.
Figure 2:
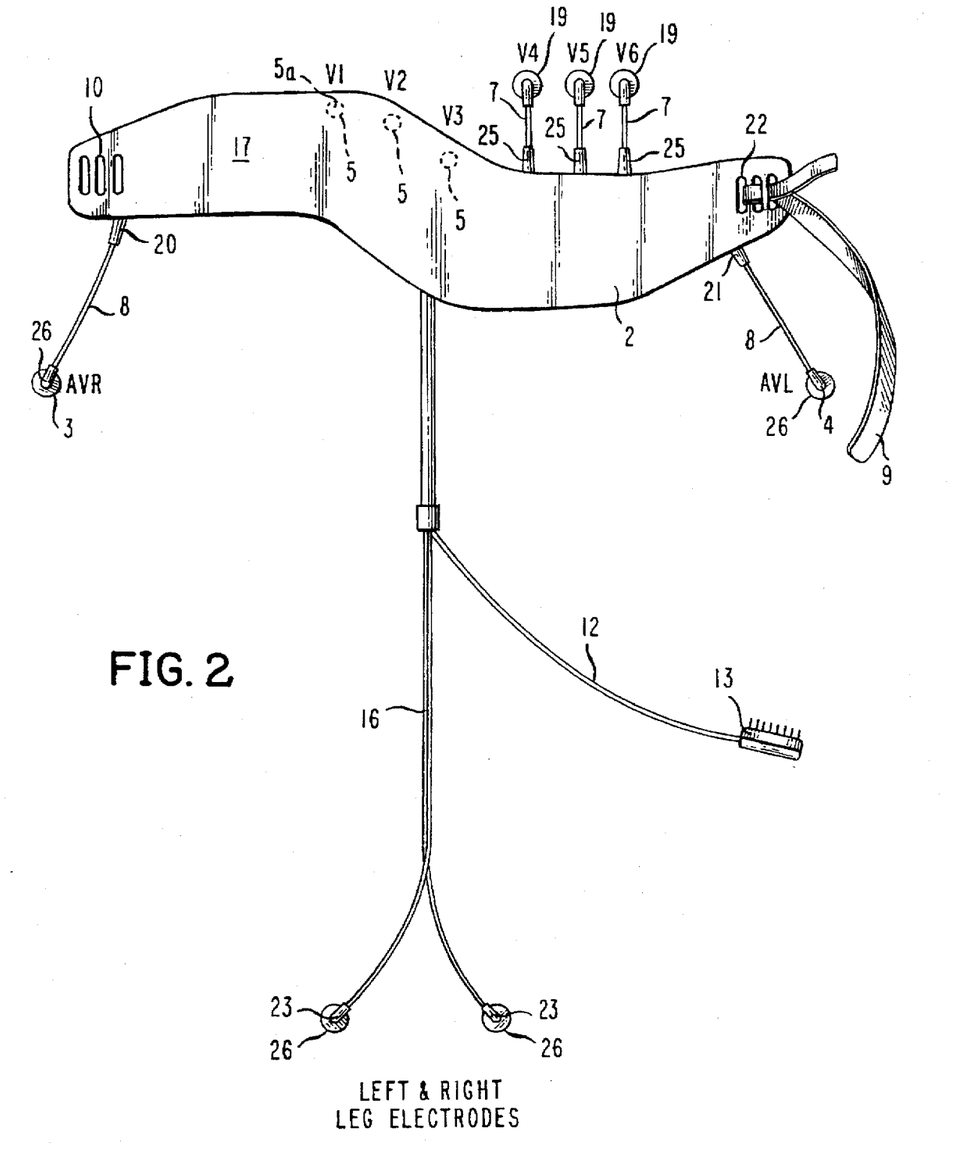
FIG. 2 is a front view of the embodiment of the electrocardiogram device of the invention illustrated in FIG. 1.
Figure 3A:
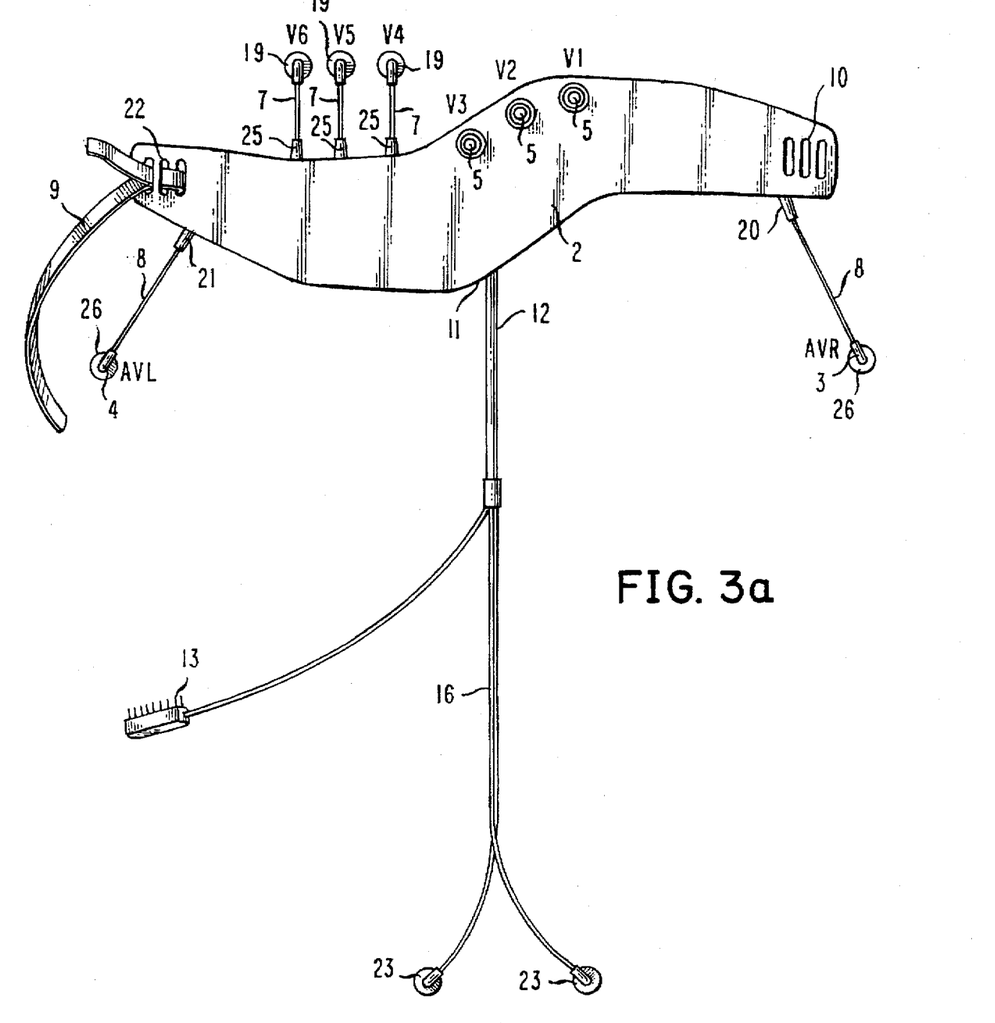
FIG. 3a back view of the embodiment of the electrocardiogram device illustrated in FIG. 1.
Figure 3B:
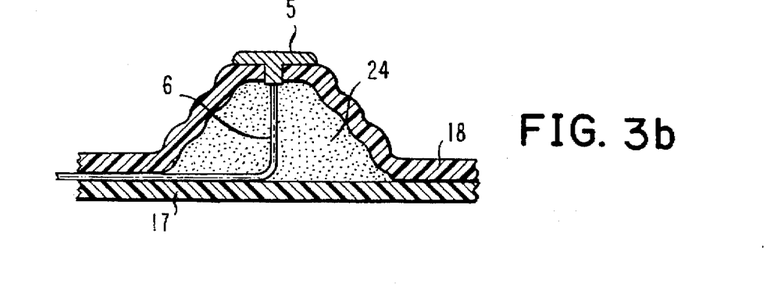
FIG. 3b is a sectional view of a fixed, raised, compressible electrode contact structure attached at $V_1$, $V_2$ or $V_3$.
Figure 4:
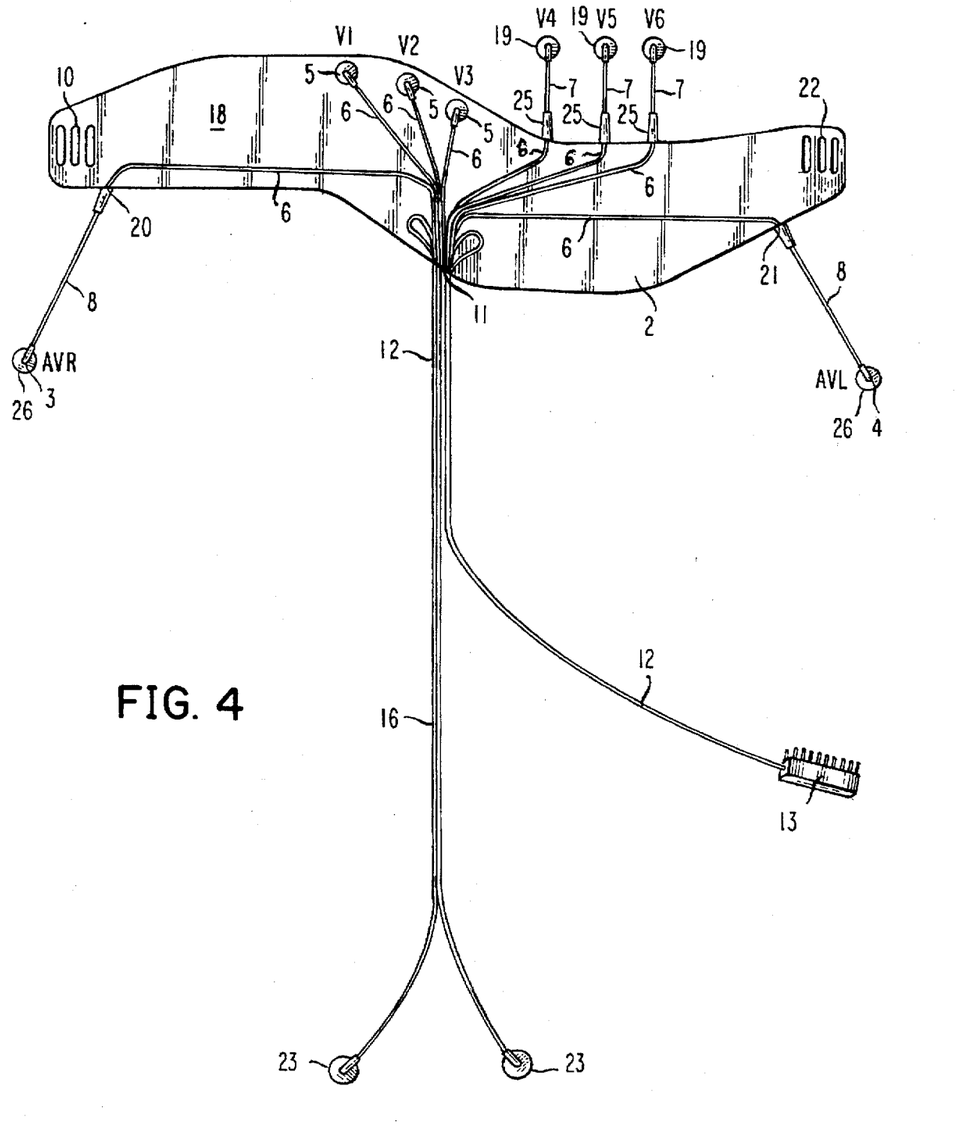
FIG. 4 is an internal view of the embodiment of the electrocardiogram device illustrated in FIG. 1 showing the leads therein.
Figure 5A:
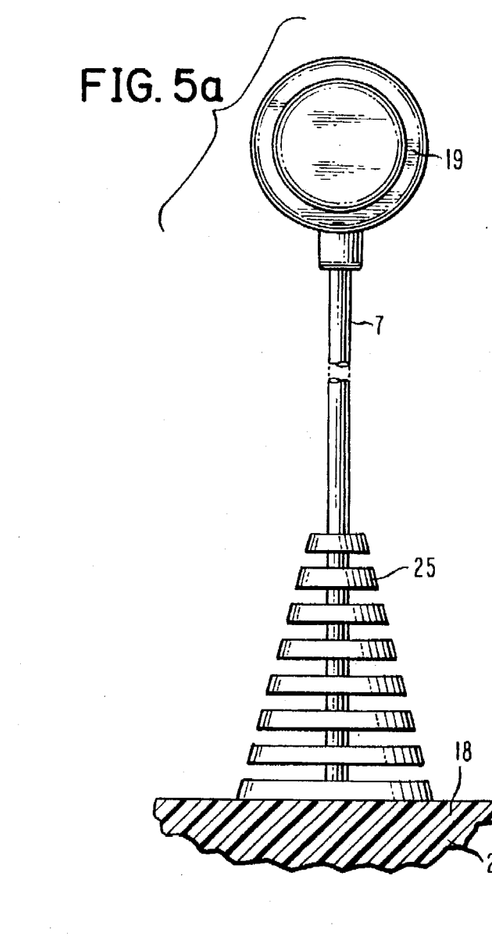
FIG. 5a is a back view of an embodiment of the movable electrode.
Figure 5B:
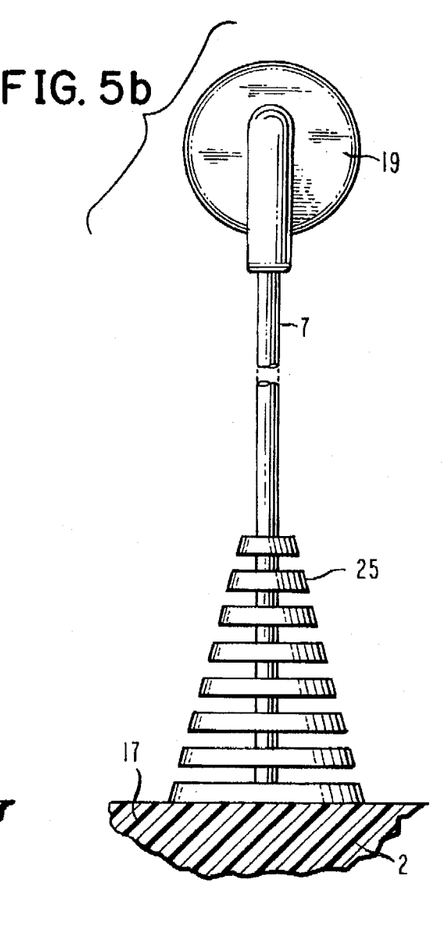
Figure 5C:
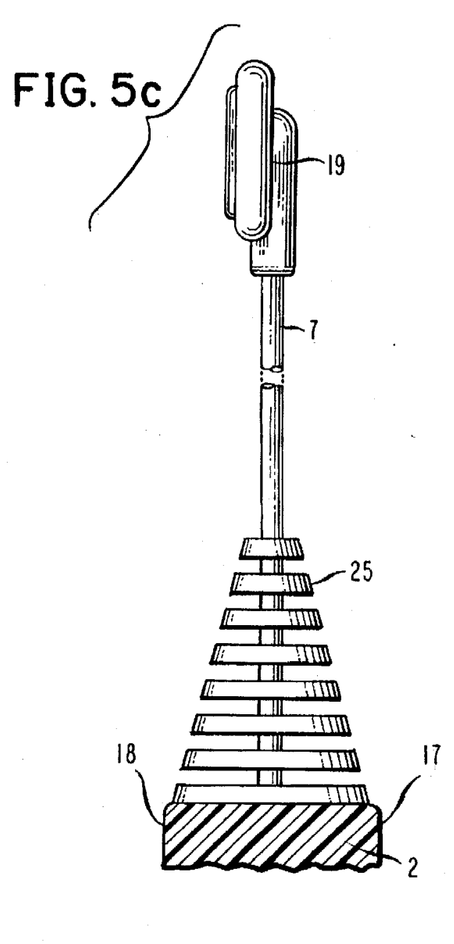

The invention can be better understood by referring to the drawings in which the preferred embodiments are illustrated. Throughout the drawings, like structures have the same numerical designations. As shown in FIGS. 1, 2, 3, 4, 6, 7 and 8, a smooth surfaced, inelastic, flexible, S-shaped or L-shaped belt-like strip 2 made of a front 17 and a back 18 flexible and shaped to cover the right breast area and arc under the left breast area in the manner that conventional leads are placed on the chest in the precordial area, thus making its perimeter reminiscent of an S- shape or an L-shape, although other shapes or configurations can be made. The strip 2 contains therein eight internal leads 6 as shown in FIG. 4 permanently attached to the inside surfaces of the front 17 and back 18 pieces. The internal leads 6 can be wires, traces or any other conventional conductor such as a wire harness as shown in FIG. 4 or a flexible circuit board. Raised, fixed contacts 5 which are spaced apart on the back surface 18 of the belt-like strip 2 are electrical conductors that make electrical conducting contact with the chest 27 of the patient usually by means of any electrolyte conducting paste conventionally used for EKG's. Fixed precordial contacts 5 are mounted on a compressible material 24 in a raised projection as shown in FIG. 3b and spaced apart on the flexible belt-like strip 2 at locations that approximately cover the places on the patient's chest 27 recognized as suitable for recording precordial electrical activity at the $V_1$, $V_2$ and $V_3$ locations. The fixed contacts 5 emerge from the back layer 18 of the belt-like strip 2. The fixed contacts 5 are in electrical conducting contact with three of the internal leads 6 in the belt-like strip 2 by means such as conventional electrical connecting means such as wire connectors, a wire harness or a flexible circuit board and are over the precordial locations $V_1$, $V_2$ and $V_3$. The fixed contacts 5 portion which faces the skin of the patient's chest 27 is embedded in a rubber or foam-like compressible material 24 in a filled projection as illustrated in FIG. 3b in cross section. The compressible material 24 provides improved skin contact between the flat electrode 5 and the normal contours of the chest surface 27. Movable precordial electrode contacts 19 are attached to external flexible electrode wires 7 which are sufficiently long to enable them to carry the electrode contacts 19 to the proper recording zones designated $V_4$, $V_5$ and $V_6$ of patients with varying body habitus'. The external electrode wires 7 which are thereon are against the belt-like strip 2 during intended usage and storage. When ready for use, the external flexible electrode wires 7 are moved so the contacts 19 thereon are on recording zones $V_4$, $V_5$ and $V_6$ on the chest 27 of the patient and between the chest 27 and the back18 of the strip 2. The external flexible wires are sufficiently long to be placed in whatever the optimum position is to provide best results. The external, flexible wires 7 are sufficiently spaced apart so that they do not become entangled. In addition, flexible supports 25 encase each external, flexible electrode wire 7 at their junction with the belt-like strip 2 in order to decrease the stress on the flexible, external electrode wires 7 and internal leads 6 during intended usage. The external electrode wires 7 and internal lead wires 6 are in electrical conducting attachment by means of conventional connectors or other means such as a wire harness or a flexible circuit board.

Figure 6:
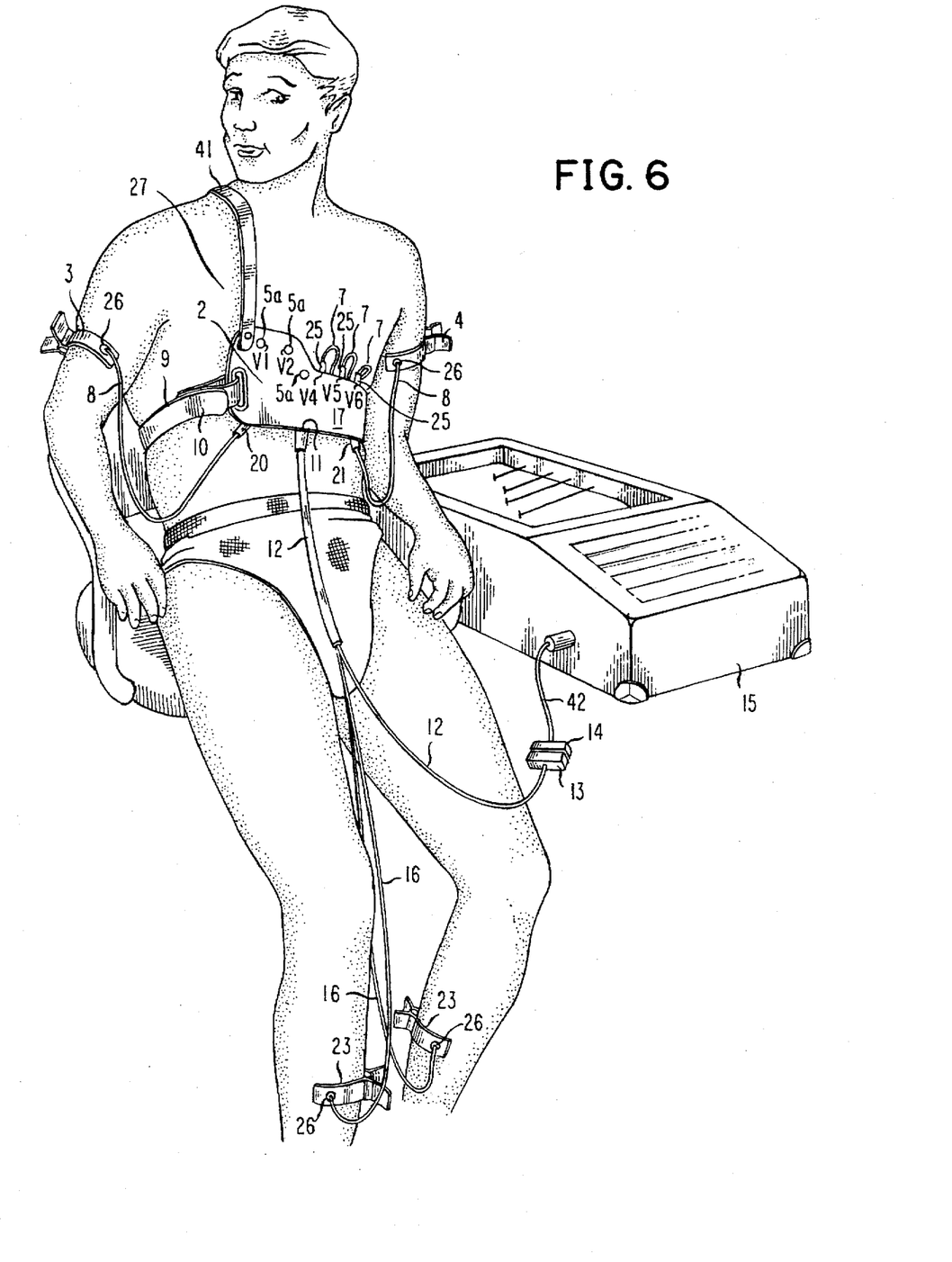
FIG. 6 depicts a second embodiment of the electrocardiogram device of the invention placed on a patient and connected to an electrocardiograph.
Figure 7:
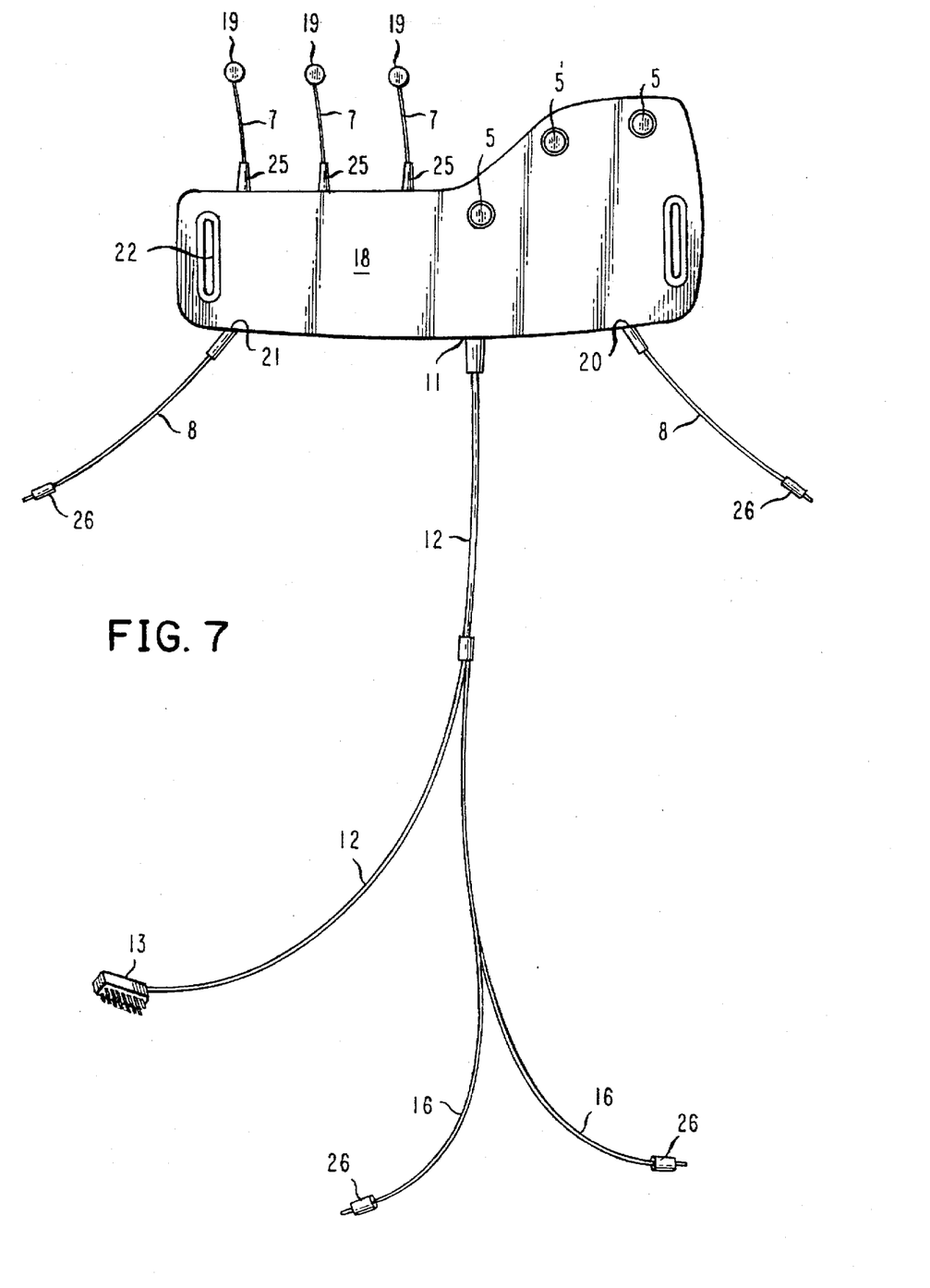
FIG. 7 is a back view of the embodiment of the electrocardiogram device illustrated in FIG. 6.
Figure 8:
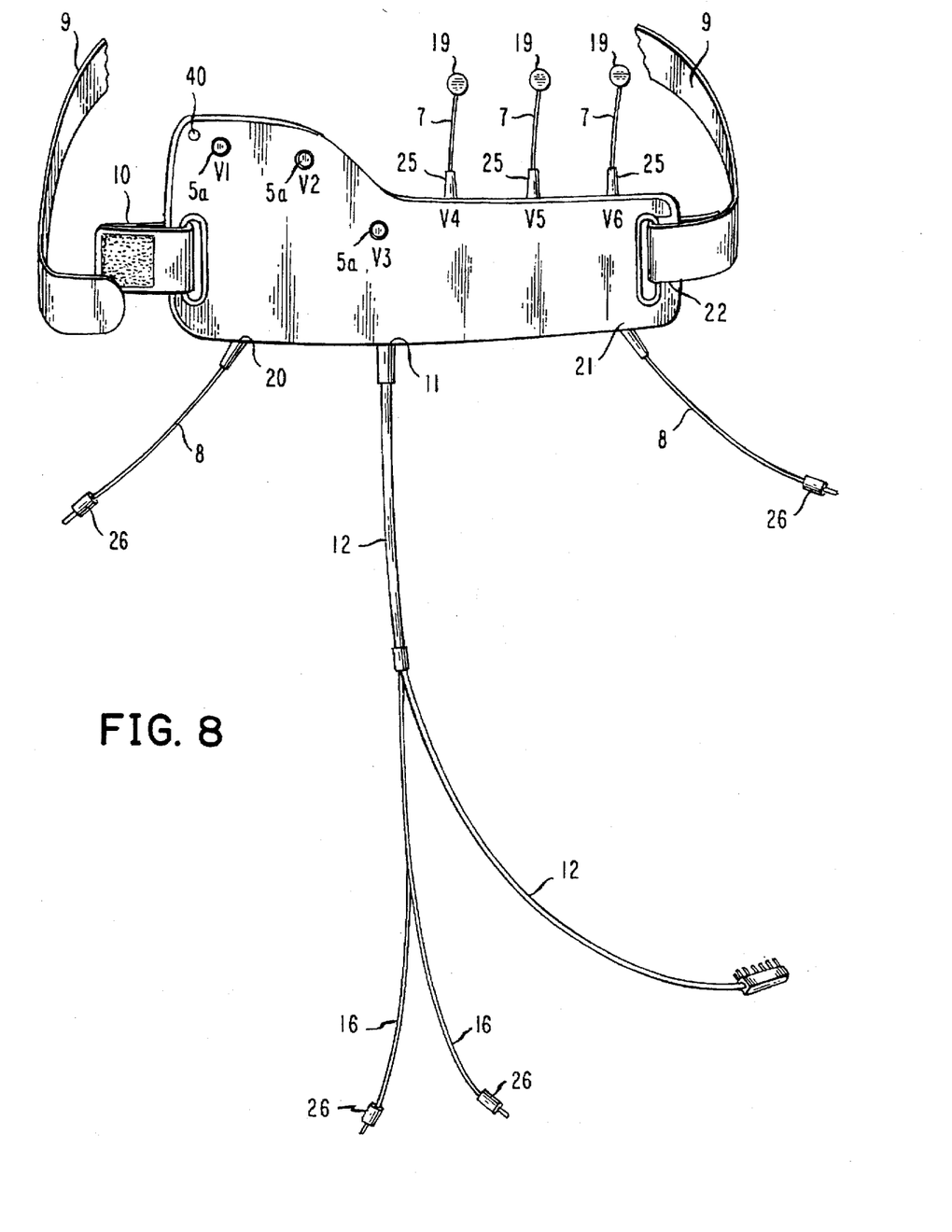
FIG. 8 is a front view of the embodiment of the electrocardiogram device illustrated in FIG. 6.

Internal leads 6 that conduct the electric signals from the fixed 5 and movable 19 precordial electrodes and the arm leads 8 to the recording electrocardiograph machine 15 are directed to an opening 11 at one place on the edge of the smooth surfaced, inelastic, flexible, S-shaped or L-shaped belt-like strip 2, exiting in cable form 12. The right 3 and left 4 arm electrode cuffs are attached to male connector plugs 26 that are attached to the ends of external arm leads 8 that are in turn are attached to internal leads 6, which attachment can be via conventional electrical connectors or other means such as a wire harness or a flexible circuit board, at openings 20 and 21 in the lower edge of the belt-like strip 2 as shown in FIG. 4. Male connector plugs 26 are attached to limb electrodes of a type chosen at the operator's discretion. The connector plugs 26 can be of any shape, however, circular plugs are commonly used. The right 3 and left 4 arm electrodes record electrical signals AVR and AVL from the right and left arms of the patient, respectively, and transmit the signals through the male connector plugs 26 through external lead wires 8 through internal leads 6 to the recording electrocardiograph 15. The external lead wires 8 are placed within the smooth surfaced, inelastic, flexible, belt-like strip 2 at openings 20 and 21 therein where they are attached to the internal leads 6. The attachment can be by any conventional means such as an electrical wire harness or a flexible circuit board. All the internal leads 6 emerge from the inelastic, flexible, belt-like strip 2 at one point 11 and are bundled into a cable 12 that attaches to that area 11 of the belt-like strip 2 that is near the base of the anteriorly placed S-like or L-like shape or any other shape used. After the smooth surfaced, inelastic, flexible, belt-like strip 2 is applied to the patient's chest 27 with the fixed precordial electrodes 5 in proper alignment over the appropriate recording zones, the belt-like strip is fastened to the patient's chest 27 by adjustably coupling the free end of an elastic strip 9 from one end 22 of the belt-like strip 2 to the closure device 10 at the other end of the inelastic, flexible, belt-like strip 2 that is nearest to the fixed electrode location $V_1$. Optionally, a shoulder strap 41 may be used to assist in holding the belt-like strip 2 on the patient. The location of the shoulder strap 41 is preferably on the right shoulder of the patient as shown in FIG. 6. It is attached by an attachment device 40 on the front upper right corner of the belt-like strip 2. A preferred attaching means is a snap or button, Velcro can also be used. The shoulder strap 41 can be attached at the patients back by means of the elastic strip 9 which holds the belt-like strip 2 on the patient, for example, with a loop.

The lower limb leads 16 are connected at one end to the cable 12 prior to its terminus and at the other end to electrode contacts 23 via the male contact plugs 26. The plugs may connect to the same variety of types of electrodes as used for the upper limbs 3, 4. The operator needs to separate only two wires 16 from the cable 12 before attaching all ten electrodes to the patient, six to the chest 27 and four to the limbs.

The cable 12 can be fixedly attached to the smooth surfaced, inelastic, flexible, belt-like strip 2 or removably attached. The free end of the cable 12 may have any suitable adapter or plug 13 for connection to an electrocardiograph machine 15 or to any appropriate adapter, plug, junction box or block 14 exiting from an electrocardiograph machine 15. Once attached, the wires 42 extending from the electrocardiograph machine 15 to the adapter, plug, junction box or block 14 do not need to be removed and reattached each time an EKG is performed. Although adapters 13 may be suitable for attachment to presently used electrocardiograph machines 15, new machines can be made to receive a plug 13 without the need to have any separate wires 42, plug, junction box or block 14 in between.

In use, the technician simply places the smooth surfaced, inelastic, flexible, belt-like strip 2 on the patient's chest 27 and adjusts the position of the marked location or locations 5a on surface 17 of the belt-like strip 2 over recording location $V_1$, $V_2$ and/or $V_3$ so the precordial electrode contacts 5 are over their proper recording areas. When present in the preferred embodiment, the marked location can be at one or more of $V_1$, $V_2$, or $V_3$. After fastening the elastic strip 9 to the clasp, buckle, Velcro pad or other attaching means 10 at the free end of the belt-like strip 2, the movable precordial electrode contacts 19 are placed over their proper recording areas, preferably between the back surface 18 of the belt-like strip 2 and the patient's chest 27. The arm lead electrodes 3, 4 are attached to the body in the usual manner and then connected to the male connector plugs 26 located on the free ends of the external flexible wire leads 8. The leg lead electrodes 23 are also attached to the body in the usual manner and then connected to the male connector plugs 26 located on the free ends of the flexible wire lower limb leads 16. The operator then applies the needed amount of an electrolyte conducting paste to the patient's chest 27 under each precordial electrode. Finally, the adapter/plug 13 or cable 12 is attached to the electrocardiograph machine 15 and the operator performs the test. Once the final attachment is made, it is not necessary to unplug the electrocardiograph machine for each successive use.

While the invention has been described with respect to illustrated embodiments for purposes of example, many variations in the construction are possible and it is not intended to limit the invention only to the illustrated embodiments.

We claim:

1. An electrocardiogram recording apparatus having fixed and movable precordial electrodes attached to lead wires, left and right arm and leg lead wires and an adapter or plug for connecting all the lead wires to an electrocardiograph machine, comprising a smooth surfaced, inelastic, flexible, belt-like strip having two ends and being L-like shape around its perimeter, said strip adapted to follow the contours of the chest of a patient in a pattern which covers the right breast and just below the left breast, wherein, raised, fixed electrodes on said belt-like strip are attached to lead wires in or on said belt-like strip wherein said raised fixed electrodes are adapted to cover precordial locations V1, V2 and V3 on the patient's chest; movable precordial electrodes attached to said belt-like strip by flexible lead wires emerging from said belt-like strip and laterally spaced from said fixed electrodes enabling the movable electrodes to be placed on precordial locations V4, V5 and V6 on the patient's chest; flexible left and right arm lead wires emerging from said belt-like strip with each having a connector plug for suitable attachment and electrical contact to conventionally used limb electrodes on each arm of the patient; a cable formed from all the lead wires emerging from the belt-like strip, said cable having two ends, the first end of which is at the emergence of the cable from the belt-like strip and the second of which is where an adapter or plug is attached to the cable, wherein each of the lead wires has two ends, one end of which forms the cable and the second of which is attached to one said electrodes, said cable having attached thereto intermediate its first end and said belt-like strip, leg lead wires with connector plugs on an end of each adapted for suitable attachment and electrical contact to conventionally used limb electrodes on each leg; an adapter or plug on the second end of said cable for connection to an electrocardiograph machine; and an elastic fastener on one of the ends of said belt-like strip for attachment to the other of the two ends of said belt-like a strip for holding said belt-like strip in place around a patient's chest.

2. The apparatus of claim 1 in which said cable is detachably attached to the lead wires emerging from said belt-like strip to allow for easier cleaning and storage of the apparatus.

3. The apparatus of claim 1 wherein the total of fixed and movable precordial electrodes is six.

4. The apparatus of claim 1 wherein said raised, fixed electrodes additionally are compressible.

5. The apparatus of claim 1 wherein said arm and leg lead wire connector plugs are circular male plugs.

6. The apparatus of claim 1 wherein said flexible belt-like strip additionally contains indicia on its surface to locate precordial locations $V_1$ and/or $V_2$ and/or $V_3$.

7. The apparatus of claim 1 additionally having a shoulder strap adapted to be connected to the right upper corner of the belt-like strip on the patient's chest and to extend over the shoulder patient's back for connection to said elastic fastener.

8. The method of claim 9 comprising placing at least one compressible fixed electrode additionally on the patient's chest.

9. A method of conducting an electrocardiogram comprising attaching the apparatus of claim 1 to the chest of a patient with the raised, fixed, precordial electrodes over recognized central precordial recording zones, placing movable precordial electrodes of the apparatus of claim 1 on recognized central and lateral precordial recording zones on said patient between the smooth surfaced, inelastic, flexible, belt-like strip and the patient's chest, attaching said arm and leg limb lead wires of the apparatus to the conventional electrodes on the arms and legs of the patient, respectively, placing an electrolyte conducting paste between and in contact with each electrode and the patient's chest, then, with the cable and any necessary adapter or plug plugged into an electrocardiograph machine, performing the electrocardiogram.

10. The method of claim 9 comprising placing at least one movable electrode on the patient's chest outside the belt-like strip.

* * * * *